United States Patent
Rasche et al.

(10) Patent No.: US 7,220,733 B2
(45) Date of Patent: May 22, 2007

(54) SEPARATION OF CRESOL FROM MARES' URINE

(75) Inventors: Heinz-Helmer Rasche, Burgdorf (DE); Kirsten Wilbrand, Wunstorf (DE); Kerstin Woltmann, Hannover (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 139 days.

(21) Appl. No.: 10/400,936

(22) Filed: Mar. 28, 2003

(65) Prior Publication Data

US 2003/0215953 A1 Nov. 20, 2003

Related U.S. Application Data

(63) Continuation of application No. PCT/EP01/11115, filed on Sep. 26, 2001.

(30) Foreign Application Priority Data

Sep. 29, 2000 (DE) .............................. 100 48 524

(51) Int. Cl.
*A61K 31/56* (2006.01)
(52) U.S. Cl. .................................... 514/170
(58) Field of Classification Search ................ 514/170
See application file for complete search history.

(56) References Cited

U.S. PATENT DOCUMENTS 4,806,245 A * 2/1989 Boddeker ................... 210/640
5,464,540 A 11/1995 Friesen et al.
5,723,454 A 3/1998 Ban et al.
5,814,624 A * 9/1998 Ban et al. ................... 514/170

FOREIGN PATENT DOCUMENTS

DE 69404958 12/1997

OTHER PUBLICATIONS

International Search Report, Dec. 27, 2002.
C.H.L. Shackleton, et al., "Use of Sep-pak® Cartridges for Urinary Steroid Extraction: Chromatographic Analysis" Clinica Chimica Acta, vol. 107, 1980, pp. 231-243.
Risto Heikkinen, et al., "Reversed-Phase $C_{18}$ Cartridge for Extraction of Estrogens from Urine and Plasma" Clin. Chem. vol. 27, No. 7, 1981, pp. 1186-1189.
H. Leon Bradlow, "Extraction of Steroid Conjugates with a Neutral Resin" Institute for Steroid Research, Montefiore Hospital and Medical Center, New York, NY, Dec. 4, 1967.

* cited by examiner

*Primary Examiner*—Barbara P. Badio
(74) *Attorney, Agent, or Firm*—Crowell & Moring LLP

(57) ABSTRACT

A method of separating cresol from mares' urine by pervaporation using pore-free polymeric silicone membranes in which starting urine solutions containing high-quality and -quantity conjugated estrogens with a reduced or substantially removed cresol content are provided which are advantageously suitable for obtaining natural mixtures of conjugated estrogens from pregnant mares' urine.

6 Claims, 2 Drawing Sheets

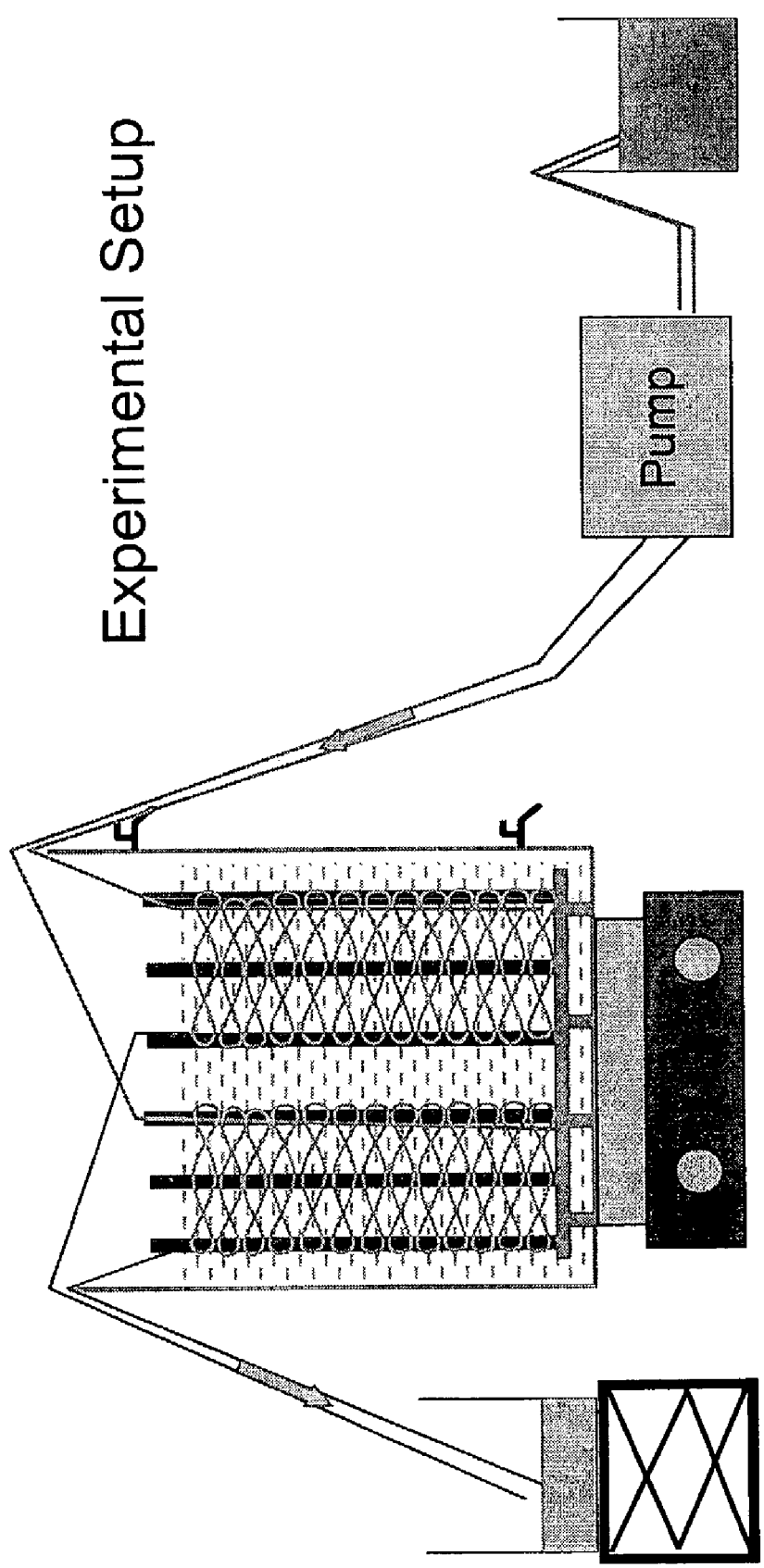

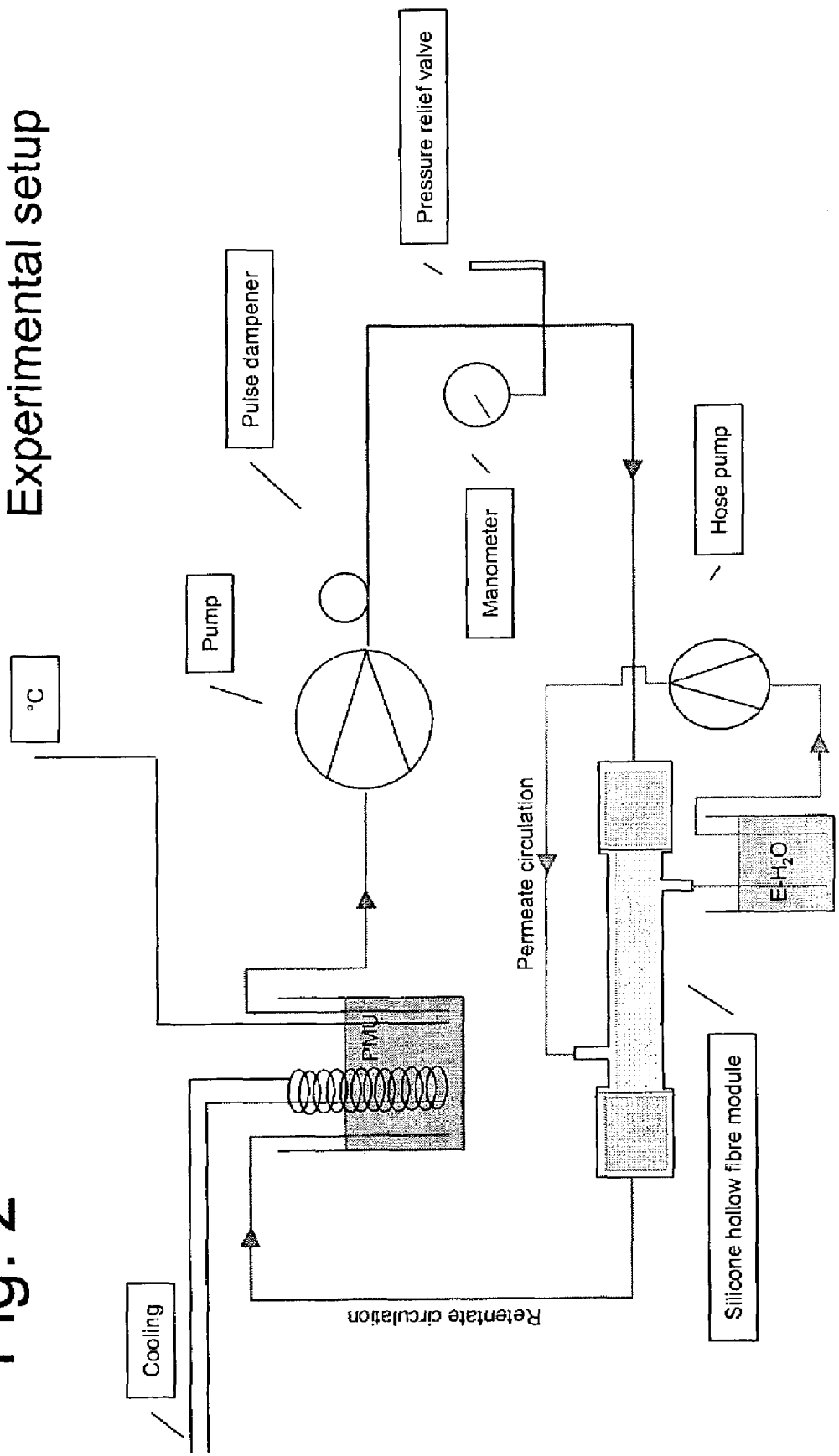
Fig. 2 Experimental setup

SEPARATION OF CRESOL FROM MARES' URINE

CROSS REFERENCE TO RELATED APPLICATIONS

This application is a continuation of international patent application no. PCT/EP01/11115, filed Sep. 26, 2001, designating the United States of America and published in German as WO 02/26760, the entire disclosure of which is incorporated herein by reference. Priority is, claimed based on Federal Republic of Germany patent application no. DE 100 48 524.3, filed Sep. 29, 2000.

BACKGROUND OF THE INVENTION

The present invention relates generally to obtaining a natural mixture of conjugated estrogens from the urine of pregnant mares, and specifically to the separation of cresol from mares' urine.

Estrogens are used in medicine for hormone replacement therapy. In particular, estrogen mixtures are used for the treatment and prophylaxis of the disorders of the climacteric period which occur in women after natural or artificial menopause. In this case, natural mixtures of conjugated estrogens such as are found in the urine of pregnant mares have proved particularly effective and readily compatible.

The dissolved solids content in the urine of pregnant mares (=pregnant mares' urine, abbreviated hereafter as "PMU") may naturally vary within wide ranges, and may generally lie in a range of 40–90 g dry substance per liter. In addition to urea and other usual urine contents, phenolic constituents are contained in the solids content of the PMU in quantities of about 2–5% by weight relative to dry matter. These phenolic constituents include cresols and dihydro-3, 4-bis[(3-hydroxyphenyl)methyl]-2(3H)-furanone, known as HPMF. These may be present in free or conjugated form. The PMU contains a natural mixture of estrogens which is largely present in conjugated form, e.g. as sulfuric acid semi-ester sodium salt (abbreviated hereafter as "sulfate salt). The content of conjugated estrogens (=conjugated estrogens, abbreviated hereafter as "CE"), calculated as estrogen sulfate salt and relative to dry matter, may be between 0.3 and 1% by weight.

Various procedures for the direct processing and obtention of the conjugated estrogens contained in the PMU are described in the prior art. Usually extracts containing conjugated estrogens are obtained from the PMU by extraction with a polar organic solvent which is not miscible, or only slightly miscible, with water, such as ethyl acetate, n-butanol or cyclohexanol. With such liquid-liquid extractions, however, a number of problems occur, such as severe foaming, sedimentation, emulsification and poor phase separation. Generally several extraction steps are required, which results in losses and only partial obtention of the estrogen content. To avoid these disadvantages, therefore, a number of solid-phase extraction methods have been proposed in the prior art.

Heikkinnen et al. (Clin. Chem. 27/7, (1981), 1186–1189) and Shackleton et al. (Clinica Chimica Acta 107 (1980), 231–243) describe a solid-phase extraction of estrogens by means of a cartridge with silanized silica gel containing octadecylsilane radicals (Sep-Pak$^R$ C$^{18}$ cartridge, manufactured by Waters Ass. Inc. Milford, Mass., USA) for the processing of small quantities of urine and plasma for analytical determination of estrogens by means of gas chromatography. Therein, the estrogens are eluted from the cartridge with methanol.

In 1968, H. L. Bradlow proposed [see Steroids 11:265–272 (1968)] to use Amberlite XAD-2$^R$, a neutral, non-polar hydrophobic polystyrene resin, manufactured by Rohm und Haas, for the extraction of conjugated estrogens from urine. The adsorption capacity quoted is low. According to Bradlow, an optionally diluted urine is passed through a column containing the resin at a low throughflow rate. The estrogens are eluted with methanol or ethanol.

More recent patent applications describe methods for obtaining an extract containing the natural mixture of conjugated estrogens from mares' urine by solid-phase extraction of the mixture of conjugated estrogens from the urine of pregnant mares e.g. on RP silica gel (WO 98/08525) or on non-ionic semipolar polymeric adsorption resins (WO 98/08526). The methods described in these international patent applications still use PMU starting materials with relatively high proportions of phenolic urine contents such as cresol and HPMF, which, although they have already been able to be separated out successfully by the method described, on the other hand limit the efficiency of the actual working-up as undesirable accompanying substances, e.g. by reducing the capacity of the respective adsorbent.

Depending on the origin of the urine or feed of the horses, a cresol content of more than 500 mg/l up to occasionally even above 1,500 mg/l may also be recorded in fresh native urine. The cresol content additionally increases according to the origin, age of the urine, degree of bacterial contamination and the storage conditions, in particular e.g. according to the storage temperature, quite conceivably to values of up to 2,000 mg/l and possibly even more. Although reliable separation of cresol is ensured for example by the alkaline washing of the adsorber column with non-ionic semipolar polymeric adsorption resins in the method in accordance with international patent application WO 98/08526, a high cresol content is disruptive for two reasons:

a) since cresol is adsorbed by the resin in addition to the hormones, the hormone capacity of the resin decreases; and b) at high cresol contents in the alkaline washing stage, a hormone loss of several percent is to be expected during this step.

In order to avoid these disadvantages, it is desirable to process urine with as low a cresol content as possible. Since low cresol contents in the PMU cannot be ensured for reasons of transportation—e.g. when the PMU is collected throughout the world, even in out-of-the-way regions—or also because of the breed of and feed given to the horses, other measures must be sought to minimize the cresol content in the PMU before the working-up and recovery of the mixtures of conjugated estrogens. Tests hitherto, e.g. adsorption tests, were not successful, since a reduction in cresol was accompanied by more or less great, unacceptable hormone losses.

In addition to the optimization, described in the prior art, of the direct, complete working-up of pregnant mares' urine (PMU) to obtain natural mixtures of conjugated estrogens (CE), therefore, also the steps preceding working-up, such as ensuring estrogen-protecting removal of undesirable accompanying substances such as cresols, are also of particular significance for effective working-up and obtaining of a high-quality and -quantity mixture of conjugated estrogens.

SUMMARY OF THE INVENTION

It is therefore an object of the present invention to provide an industrial method for the separation of cresols from PMU which delivers a PMU which is largely depleted in cresol. Such PMUs which have been largely freed from cresol represent a high-quality and -quantity starting material for the actual working-up to obtain the natural mixture of conjugated estrogens from the PMU.

A method has now been discovered which represents a special type of filtration, what is called pervaporation, and with which the cresol content of pregnant mares' urine (PMU) can be reduced simply and effectively. The method according to the invention for the separation of cresol from pregnant mares' urine (PMU) is distinguished in that the cresol content of an aqueous starting solution of PMU is reduced by pervaporation by means of a pore-free polymeric silicone membrane, by permeating cresol to the permeate side of the membrane and obtaining the treated PMU solution as retentate with reduced cresol content containing a mixture of conjugated estrogens.

Pervaporation is a special type of filtration in which one constituent of a liquid mixture (starting solution) is transported from the feed side of a pore-free, polymeric membrane to the permeate side. This frequently involves a change of phase from liquid to gaseous (gas space or vacuum), but there may also be a transition from a liquid phase of the starting solution from which a given substance is to be separated into a second liquid phase which receives the substance to be separated on the permeate side. The membrane represents an almost complete barrier to the rest of the constituents of the mixture or starting solution.

Selective transport of the substance to be separated from a mixture occurs if the concentrations of this mixture constituent are different in the feed and in the membrane. The separating effect is based on the interaction of the permeating mixture constituent, i.e. the constituent which is to be separated out, with the membrane used, which is capable of selectively sorbing the mixture constituent which is to be separated out, diffusing it through the membrane and desorbing it on the permeate side. It was discovered according to the invention that pore-free polymeric silicone membranes are excellently suited to reducing or largely separating cresol from pregnant mares' urine (PMU), with the desired conjugated estrogens contained in the PMU, such as estrone and equilin, remaining completely in the retentate so as to protect the product.

Within the scope of the invention, any desired pervaporation installation which is equipped in some form with one or more pore-free polymeric silicone membranes may be used.

In one variant of the method according to the invention for separating cresol from pregnant mares' urine (PMU), the reduction in the cresol content of an aqueous starting solution of PMU by pervaporation is achieved by pumping the cresol-containing aqueous starting solution of PMU through a silicone tube acting as a pore-free polymeric membrane or a silicone hollow fiber module, with cresol being permeated on the permeate side and the treated PMU solution being obtained as a retentate containing a mixture of conjugated estrogens with reduced cresol content.

In the variants of the method according to the invention described above, a vacuum, a gas phase or a cresol-receiving permeate liquid may be present on the permeate side. A preferred embodiment of the method according to the invention is distinguished in that a permeate liquid, in particular water or an aqueous ethanolic solution, is present on the permeate side. In this case, it has proved advantageous if the cresol-receiving permeate liquid is replenished at intervals or continuously during the pervaporation. This means that a beneficial driving concentration gradient can be maintained.

Pore-free polymeric membranes made of very widely-varying silicone types can be used in the method according to the invention. Advantageously, for example, pore-free polymeric membrane silicones such as are available as industrial products (see e.g. Winnacker-Küchler (3.) 5:252–286). Such silicones belong to an extensive group of synthetic polymeric organo-silicon compounds in which silicon atoms are linked via oxygen atoms and the remaining valencies of the silicon are saturated by hydrocarbon radicals (e.g. usually methyl radicals, but occasionally also other radicals such as ethyl, propyl or phenyl groups). Worthy of mention are e.g. "silicone rubbers", e.g. high-temperature vulcanizing silicone rubber compounds ("hot rubber"), which are for the most part plastically deformable materials, yet which are still able to flow, which by vulcanization produce a heat-resistant elastic silicone rubber, which can be processed further to give materials for very widely ranging purposes, in particular e.g. to produce silicone rubber tubes which can be used in the chemical industry and in medicine.

The concrete configuration in each case of the method according to the invention within the context of the boundary conditions existing in the individual case should not cause the person skilled in the art any particular problems. In particular, the optimum process conditions in each case be can determined by a few preliminary tests, for example of the type such as explained further below by the examples according to the invention.

The invention has the advantage that due to the removal of cresol the specific volume of urine which can be charged per litre of resin on to a column for separation and isolation of conjugated estrogens is increased. This means that during the subsequent working-up proper of PMU on a resin column the undesirable adsorption of cresol on the resin (e.g. on the ion-exchange resin XAD-7 which is frequently used) is avoided and the capacity additionally obtained is utilized for the adsorption of the valuable hormone constituents. Furthermore, the reduction in the cresol content in PMU also has an advantageous effect on minimizing the hormone losses during the working-up of the PMU, e.g. in alkaline column washing (see e.g. WO 98/08526).

BRIEF DESCRIPTION OF THE DRAWINGS

The invention will be described in further detail hereinafter with reference to illustrative preferred embodiments carried out using apparatus shown in the accompanying drawing figures in which:

FIG. 1 is an outline of an experimental setup for liquid-liquid extraction of cresol from PMU by pervaporation through a silicone tube as pore-free polymeric membrane; and FIG. 2 is an outline of an experimental setup for liquid-liquid extraction of cresol from PMU by pervaporation using a silicone hollow fiber module.

EXAMPLES

The following examples are intended to explain the invention further, but without limiting its scope.

Principle of Pervaporation

Pervaporation is a special type of filtration in which one constituent of a liquid mixture (starting solution) is transported from the feed side of a pore-free, polymeric membrane to the permeate side. This frequently involves a change of phase from liquid to gaseous (gas space or vacuum), but a transition from a liquid phase of the starting solution from which a given substance is to be separated into a second liquid phase which receives the substance to be separated out on the permeate side may also occur. The membrane represents an almost complete barrier to the rest of the constituents of the mixture or starting solution.

Selective transport occurs if the concentrations of the mixture constituents in the feed and in the membrane are different. The separating effect is based on the interaction of the permeating mixture constituent, i.e. the constituent which is to be separated out, with the membrane used, which is capable of selectively sorbing the mixture constituent which is to be separated out, diffusing it through the membrane and desorbing it on the permeate side.

In the following tests of Example 1 a pervaporation installation was used, to the permeate side of which a stream of liquid was offered. The method according to Example 1 is not to be understood as being restrictive, since it is also possible to operate in pervaporation installations which have a gas space or vacuum on the permeate side for receiving the substance to be separated out. Another procedure, using a hollow fiber module, which likewise is not to be understood as being restrictive, is shown in Example 3.

Example 1

Pervaporation Tests (Liquid-liquid, Silicone Tube)

In the following pervaporation tests of this example, a experimental setup consisting of tubes (membrane) and surrounding stream of liquid (permeate side) was used. The experimental setup is outlined in FIG. 1. Since it is desirable to start with a large specific surface area of the membrane, tubes with an internal diameter of approx. 1 mm and a wall thickness of approx. 0.4 mm were used.

Test 1:

Urine in a volume of 30 ml/h was pumped from a receiving solution through a silicone tube 25 m in length. The tube was rolled up in a bowl filled with 1 liter of 30% strength ethanolic solution. Analysis showed that only cresol is depleted in the urine and diffuses into the ethanolic solution (permeate). The results are shown in the following Table 1.

TABLE 1

|  | Estrone (mg/l) | Equilin (mg/l) | Cresol (mg/l) | HPMF (mg/l) |
|---|---|---|---|---|
| Starting urine solution | 41.5 | 15.8 | 89.4 | 1.2 |
| Tube discharge after 1 h (retentate) | 41.4 | 16.0 | 15.5 | 1.5 |
| Tube discharge after 4 h (retentate) | 41.4 | 15.9 | 10.9 | 1.5 |
| Ethanolic solution after 4 h (permeate) | 0 | 0 | 9.8 | 0 |

Test 2:

The test was performed as previously in Test 1, except that the ethanolic solution was replaced with demineralized water. Analysis showed in principle the same picture as in Test 1. In this test too, cresol diffused into the aqueous phase serving as permeate. No losses of estrone and equilin occurred. The results are shown in the following Table 2.

TABLE 2

|  | Estrone (mg/l) | Equilin (mg/l) | Cresol (mg/l) | HPMF (mg/l) |
|---|---|---|---|---|
| Starting urine solution | 41.5 | 15.8 | 89.4 | 1.2 |
| Tube discharge after 7 h (retentate) | 42.8 | 16.4 | 16.0 | 1.3 |
| Aqueous phase after 7 h (permeate) | 0 | 0 | 16.2 | 0 |

Test 3:

The test arrangement of tests 1 and 2 was extended to four parallel tubes each 25 m in length. The initial urine had a high cresol content. The experimental setup is illustrated by way of example in FIG. 1. A 25 m silicone tube (internal diameter 1 mm, wall thickness 0.4 mm) was wound onto each of the four struts, and the struts were then placed in a container. Each of the four tubes was connected individually to a hose pump. On the permeate side, i.e. on the outside around the tubes, there was 8 liters of an aqueous ethanol solution, which was stirred. Thereafter, the PMU starting solution was pumped at 8 rpm (=15.6 ml/h) through the tubes. Per tube, in each case for a time interval of 2 h the retentate (=treated PMU) was collected, and the concentrations of the constituents of these fractions were determined. The test was ended after 6 hours, i.e. after the third fraction. The total quantity of PMU which was passed through all four tubes was approx. 374 ml in 6 hours, which corresponds to a total of 232 mg cresol. The total cresol in 8 liters of aqueous permeate after 6 hours was 307 mg.

Analysis of the constituents in the retentate and permeate yielded the same picture as previously obtained in Tests 1 and 2. Estrone and equilin were retained, and 95% of the cresol was removed. The results of Test 3, removal of cresol by liquid-liquid extraction by silicone tube pervaporation, are shown in the following Table 3.

TABLE 3

| Sample | DM Content | PH Value | Equilin [mg/l] | Estrone [mg/l] | Cresol [mg/l] | HPMF [mg/l] |
|---|---|---|---|---|---|---|
| Reference | 5.82 | 8.04 | 25.7 | 17.2 | 620.2 | 129.3 |
| Tube 1, 2 h | 5.81 | 8.63 | 26.8 | 17.6 | 32.2 | 110.5 |
| Tube 2, 2 h | 5.87 | 8.63 | 27.8 | 17.8 | 35.6 | 111.2 |
| Tube 3, 2 h | 5.78 | 8.65 | 28.5 | 18.6 | 32.2 | 109.7 |
| Tube 4, 2 h | 5.78 | 8.69 | 28.0 | 18.4 | 37.1 | 108.3 |
| Tube 1, 4 h | 5.91 | 8.62 | 28.1 | 18.1 | 36.4 | 112.4 |
| Tube 2, 4 h | 5.82 | 8.61 | 28.4 | 19.8 | 36.2 | 109.1 |
| Tube 3, 4 h | 5.82 | 8.61 | 26.3 | 18.7 | 32.5 | 115.0 |
| Tube 4, 4 h | 5.79 | 8.61 | 27.7 | 18.4 | 35.8 | 111.4 |
| Tube 1, 6 h | 5.81 | 8.59 | 28.0 | 18.5 | 46.1 | 111.5 |
| Tube 2, 6 h | 5.73 | 8.59 | 28.8 | 17.8 | 45.2 | 110.3 |
| Tube 3, 6 h | 5.76 | 8.59 | 28.3 | 19.9 | 44.4 | 114.7 |
| Tube 4, 6 h | 5.89 | 8.59 | 28.8 | 19.3 | 47.7 | 111.7 |
| Permeate, test end | 0.00 | 5.55 | 0.0 | 0.0 | 38.4 | 0.0 |

The increase in the cresol values in the individual tubes after 2 hours and 4 hours is probably due to a concentration of cresol in the receiving aqueous phase. Due to this, the drop in concentration driving the permeation is reduced. If desired, the volume may be increased or the permeate replaced more frequently for counter-controlling.

Result of Tests 1 to 3:

The pore-free silicone membrane investigated in Example 1 is suitable for the selective separation of cresol from mares' urine. Estrone and equilin were retained completely. In principle, this provides a method for reducing high cresol contents in PMU of widely varying origins and thereby increasing the hormone capacity of adsorber columns in the subsequent working-up of the PMU to obtain mixtures of conjugated estrogens and minimising the washing losses of conjugated estrogens which otherwise occur.

Example 2

Comparison Example

Of five pore-free membranes investigated, only silicone was suitable for the selective separation of cresol from mares' urine in which estrone and equilin were completely retained.

In initial tests, in addition to silicone the following materials in the form of tubes were also investigated analogously to Example 1 (Tests 1 and 2): polyethylene (PE), polyvinyl chloride (PVC), cellulose (2 tests). Without going into further details, the following results were obtained for these materials. For PE and PVC, no diffusion of cresol, HPMF and estrone took place. For the two different cellulose dialysis tubes investigated, cresol and estrone partially diffused, but HPMF did not. Only silicone tubes, as shown in Example 1, allowed only cresol to pass selectively.

Example 3

Pervaporation Tests (Silicone Hollow Fiber Module)

In the pervaporation test of this example, an installation with a module of hollow silicone fibers was used comprising 100 capillaries having an internal diameter of 0.005 m and a length of 30 cm. A pervaporation surface totaling 0.09425 m² was available. The experimental setup is depicted in FIG. 2. The test was run at a temperature of 19° C. under conditions analogous to Example 1, and sampling took place after 3 hours. The results of the removal of cresol from PMU with the silicone hollow fiber module are shown in the following Table 4.

TABLE 4

|  | Estrone (mg/l) | Equilin (mg/l) | Cresol (mg/l) | HPMF (mg/l) |
| --- | --- | --- | --- | --- |
| Starting urine solution | 13.0 | 27.4 | 770.8 | 12.5 |
| Retentate after 3 h | 12.6 | 26.9 | 545.5 | 11.7 |
| Permeate after 3 h | 0.0 | 0.0 | 8.9 | 0.0 |

The foregoing description and examples have been set forth merely to illustrate the invention and are not intended to be limiting. Since modifications of the described embodiments incorporating the spirit and substance of the invention may occcur to persons skilled in the art, the invention should be construed broadly to include all variations falling within the scope of the appended claims and equivalents thereof.

What is claimed is:

1. A method for separating cresol from pregnant mares' urine, comprising reducing the cresol content of an aqueous starting solution of pregnant mares' urine by pervaporation using a pore-free polymeric silicone membrane, by permeating cresol on to a permeate side of the membrane, wherein a permeate liquid is present on the permeate side of the membrane, and obtaining a treated pregnant mares' urine solution as a retentate containing a mixture of conjugated estrogens with reduced cresol content.

2. A method according to claim 1, wherein the cresol content of an aqueous starting solution of pregnant mares' urine is reduced by pervaporation, by pumping the cresol-containing aqueous starting solution of pregnant mares' urine through a silicone tube acting as a pore-free polymeric membrane or through a module of hollow silicone fibers, with cresol being permeated on to the permeate side, wherein a permeate liquid is present on the permeate side of the membrane, and the treated pregnant mare's urine solution being obtained as a retentate containing a mixture of conjugated estrogens with reduced cresol content.

3. A method according to claim 1, wherein the permeate liquid comprises water.

4. A method according to claim 1, wherein the permeate liquid comprises an aqueous ethanolic solution.

5. A method according to claim 1, wherein the cresol-receiving permeate liquid is replenished at intervals during the pervaporation.

6. A method according to claim 1, wherein the permeate liquid is replenished continuously during the pervaporation.

* * * * *